United States Patent [19]

Murib

[11] 4,271,080

[45] Jun. 2, 1981

[54] PROCESS FOR THE PREPARATION OF TETRAHYDROFURAN

[75] Inventor: Jawad H. Murib, Cincinnati, Ohio

[73] Assignee: National Distillers and Chemical Corp., New York, N.Y.

[21] Appl. No.: 159,977

[22] Filed: Jun. 16, 1980

[51] Int. Cl.³ .......................................... C07D 307/08
[52] U.S. Cl. ............................... 260/346.11; 570/237; 570/241; 570/256; 570/101
[58] Field of Search ........... 260/346.11, 654 R, 654 H

[56] References Cited

U.S. PATENT DOCUMENTS 3,931,238  1/1976  Starks ............................... 260/346.11

Primary Examiner—Richard Raymond
Attorney, Agent, or Firm—Kenneth D. Tremain

[57] ABSTRACT

Tetrahydrofuran is prepared by reacting a 1,4-dihalobutane with water in the vapor phase in the presence of a catalytically effective amount of at least one solid acidic elemental oxide and/or solid acidic mixed elemental oxide, or acidic ion exchange resin which is stable under reaction conditions.

10 Claims, No Drawings

4,271,080

PROCESS FOR THE PREPARATION OF TETRAHYDROFURAN

This application relates to subject matter disclosed in commonly assigned copending U.S. patent application Ser. Nos. (159,979; 159,978; and 159,180) filed of even date herewith, respectively entitled "Process for the Preparation of Glycols", "Process for the Preparation of Tetrahydrofuran" and "Process for the Preparation of Tetrahydrofuran".

BACKGROUND OF THE INVENTION

1. Field of the Invention

This invention relates to tetrahydrofuran, and in particular, relates to the manufacture of tetrahydrofuran from 1,4-dihalobutane.

2. Description of the Prior Art

Tetrahydrofuran is a cyclic ether finding wide and substantial use as a solvent for natural and synthetic resins, especially the vinyl resins, in coatings, adhesives, printing inks, as a chemical intermediate and as a monomer. Tetrahydrofuran has been prepared via the catalytic hydrogenation of furan, from the reaction of acetylene and formaldehyde and from the dehydrocyclization of 1,4-butanediol or dehydrochlorocyclization of 4-chloro-1-butanol. The last mentioned cyclization processes are of particular interest since they employ as starting materials aliphatic derivatives which are relatively abundant and inexpensive (viz., U.S. Pat. Nos. 2,950,232; 3,467,679; 3,726,905; 4,002,646; and, 4,093,633). Heretofore, no attempt has been made to utilize the 1,4-dihalobutanes as starting materials for conversion to tetrahydrofuran since these compounds would first have to be converted to a 4-chloro-1-butanol or 1,4-butanediol preparative to the cyclization to the cyclic ether.

SUMMARY OF THE INVENTION

It has now been surprisingly discovered that if a 1,4-dihalobutane is reacted with water in the vapor phase in the presence of certain solid acidic elemental oxides or mixed elemental oxides as catalysts, tetrahydrofuran is produced. Thus, in accordance with the present invention, a process is provided for preparing tetrahydrofuran which comprises reacting a 1,4-dihalobutane with water in the vapor phase in the presence of a catalytically effective amount of at least one solid acidic elemental oxide and/or solid acidic mixed elemental oxide, or an acidic ion exchange resin which is stable under reaction conditions. The term "mixed elemental oxide" is used herein to refer to combinations of two or more elemental oxides, themselves known in the art, wherein the individual oxides are present in a more intimate relationship than that which can be obtained with mere mechanical mixing.

While not wishing to be bound in any way, it would appear that the aforesaid reaction at first hydrolyzes the 1,4-dihalobutane to the corresponding 1,4-chlorohydrin and/or 1,4-butanediol, which thereafter cyclize to tetrahydrofuran. Regardless of the actual mechanism or reaction sequence by which 1,4-dihalobutanes are converted to tetrahydrofuran in accordance with this invention, it remains that the starting compounds herein can be employed as a source for this commercially important cyclic ether without having to proceed through a series of distinct reactions each requiring a separate operation. Accordingly, the process of this invention provides a simple route to tetrahydrofuran utilizing inexpensive and readily available raw materials.

The process of this invention is especially advantageous when employing a 1,4-dihalobutane derived from butadiene by halogenation followed by hydrogenation since the halogen for this reaction can be obtained by oxidizing the by-product haloacid obtained from the hydrolysis herein of 1,4-dihalobutane to provide tetrahydrofuran. Illustrating the overall sequence of steps for such a synthetic route to tetrahydrofuran, the reactions are:

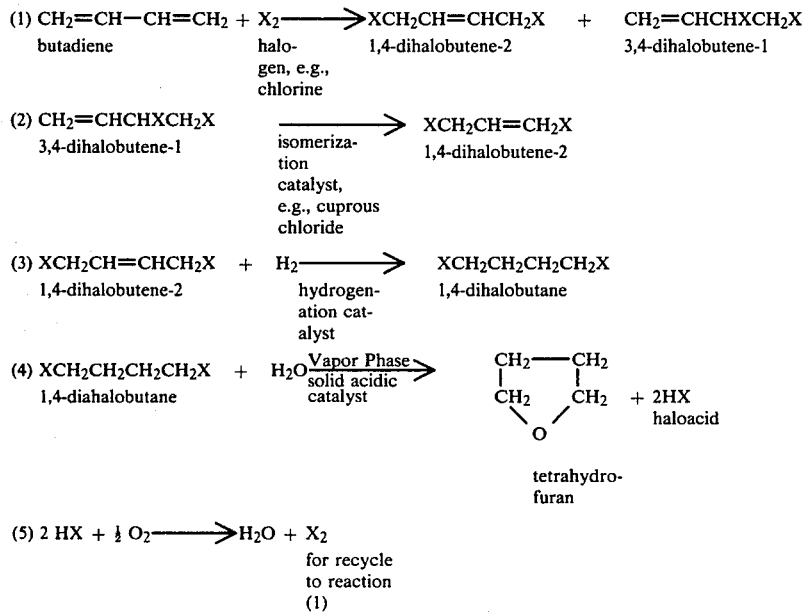

From the above, it will be seen that starting with butadiene, the only additional reactants which are consumed in obtaining tetrahydrofuran are hydrogen and oxygen (advantageously from air). Unlike the process of U.S. Pat. No. 4,093,633 referred to supra, the process of this invention does not require expensive metallic catalysts such as palladium or tellurium. In addition, the process herein utilizes only one mole of halogen compared to two moles of acetic acid for the process of U.S. Pat. No. 4,093,633.

DESCRIPTION OF THE PREFERRED EMBODIMENTS

Among the 1,4-dihalobutanes which can be used herein with good results are included 1,4-dichlorobutane, 1,4-dibromobutane, 1-chloro-4-bromobutane, 1-chloro-4-iodobutane, and the like. The 1,4-dihalobutanes can be used singly or in admixture. 1,4-dichlorobutane is especially preferred herein due to its relatively low cost and ready availability.

The reaction of the 1,4-dihalobutane and steam can be carried out with less than the stoichiometrically required amount of water but it is generally preferable to use a large stoichiometric excess of water, e.g., from about 1.5 to about 10 times the amount calculated.

The vapor phase hydrolysis reaction herein is carried out in the presence of a solid acid such as acidic elemental oxides, mixed elemental oxides, or acidic ion exchange resins. Among the useful elemental oxides and/or mixed metal oxides which can be used herein include oxides of aluminum, silicon, titanium, vanadium, zinc, zirconium, molybdenum, iron, tin, boron, cobalt, nickel, tungsten, and the like. Also useful in the process described herein are certain acidic ion exchange resins which are stable under reaction conditions, e.g., sulfonated styrene-divinylbenzene copolymer resins such as Amberlite IR-120, Amberlite IR-200 (Rohm & Haas), Dowex 50 W, Dowex MPC-1 (Dow Chemical Co.), Duolite C-20, Duolite CS-100 (Diamond Alkali Co.), Ionac C-240 and Ionac C-250 (Ionac Chemical Co.). Especially preferred herein due to its relatively low cost and ready availability are mixed oxides of aluminum and silicon. The amount of catalyst which can be used can vary over fairly wide limits and in general should be sufficient to provide a contact time from about 1 to about 150 seconds, and advantageously from about 5 to about 100 seconds.

The process conditions are not overly critical with regard to ranges of temperature and pressures employed provided however, that vapor phase reaction conditions be maintained. The practical limitations of production equipment will dictate to a great extent the selection of temperatures and pressure at which the reaction is to be effected. Thus, using available production systems, the selected temperature should be at least about 175° C. and can range up to about 350° C. and even higher. For most purposes, the preferred operating temperature ranges from about 200° C. to about 300° C. The pressure, while not critical, should be such that a vapor reaction mixture is maintained in the reactor zone, particularly when employing the aforesaid preferred temperature range.

Recovery of the product tetrahydrofuran can be accomplished by any of the known and routine techniques, e.g., distillation.

The following examples are further illustrative of the process of this invention for the preparation of tetrahydrofuran.

EXAMPLE 1

Catalyst: $SiO_2$-$Al_2O_3$

A pyrex reactor 25 cm×2.8 cm (inside diameter) provided with a thermowell and thermocouple was packed with 65.2 g catalyst (bulk volume 110 ml), containing 75 weight percent silica and 25 weight percent alumina. A vapor mixture of 9.2 mole percent 1,4-dichlorobutane, 32.5 mole percent steam and 58.3 moles percent nitrogen was fed through the catalyst at 204° C. and 37 second contact time. The reactor effluent was passed through a U-tube held at dry-ice temperature. Analysis of the condensate by gas-liquid chromatograph (GLC) disclosed formation of tetrahydrofuran in 94% selectivity at 35% conversion per pass. Mass spectral analysis of the product gave cracking patterns identical to that of an authentic sample of tetrahydrofuran.

EXAMPLE 2

Catalyst: $MoO_3$-$TiO_2/Al_2O_3$

Example 1 was repeated except that the catalyst contained mixed oxides of molybdenum and titanium supported on alumina. The reactor was packed with 57.6 g of this catalyst (bulk volume 50 ml) containing 12 weight percent Mo and 5 weight percent Ti. A mixed vapor feed of 20.2 mole percent 1,4-dichlorobutane, 72.1 mole percent steam and 7.7 mole percent nitrogen was passed through the catalyst at 260° C. and 51 second contact time. Tetrahydrofuran was obtained in 95% selectivity at 15.4% conversion per pass. When the reactor temperature was raised to 300° C., the conversion increased to 85% but the selectivity decreased to 47%.

EXAMPLE 3

Catalyst: $Al_2O_3$

Example 2 was repeated except that the catalyst contained alumina heated at 268° C. Tetrahydrofuran was obtained in practically quantitative selectivity at 9% conversion. Operation at 293° C. increased the conversion to 25.2% per pass without loss in selectivity.

What is claimed is:

1. A process for preparing tetrahydrofuran which comprises reacting a 1,4-dihalobutane with water in the vapor phase in the presence of a solid acid catalyst.

2. The process of claim 1 wherein the 1,4-dihalobutane is 1,4-dichlorobutane.

3. The process of claim 1 wherein water is present in stoichiometric excess.

4. The process of claim 1 wherein the temperature of the reaction mixture is from about 175° C. to about 350° C.

5. The process of claim 4 wherein the temperature of the reaction mixture is from about 200° C. to about 300° C.

6. The process of claim 1 wherein the solid acid catalyst is an acidic elemental oxide, mixed acidic elemental oxides, or an acidic ion exchange resin which is stable under reaction conditions.

7. The process of claim 6 wherein the solid acid catalyst is aluminum oxide.

8. The process of claim 6 wherein the solid acid catalyst is mixed aluminum and silicon oxides.

9. A process for preparing tetrahydrofuran which comprises:

(a) reacting butadiene with halogen to provide a mixture of 1,4-dihalobutene-2 and 3,4-dihalobutene-1;
(b) isomerizing the 3,4-dihalobutene-1 from step (a) to 1,4-dihalobutene-2;
(c) reacting the 1,4-dihalobutene-2 from steps (a) and (b) with hydrogen in the presence of a catalytically effective amount of at least one hydrogenation catalyst to provide 1,4-dihalobutane;
(d) reacting the 1,4-dihalobutane from step (c) with water in the vapor phase in the presence of a solid acid catalyst selected from the group consisting of solid acidic elemental oxides, mixed solid acidic elemental oxides, and acidic ion exchange resins which are stable under reaction conditions to provide tetrahydrofuran and by-product hydrohalic acid;
(e) reacting the by-product hydrohalic acid from step (d) with oxygen to provide halogen; and,
(f) recycling the halogen from step (e) to react with a fresh quantity of butadiene in step (a).

10. The process of claim 9 wherein the halogen is chlorine.

* * * * *